United States Patent [19]

Kim et al.

[11] Patent Number: 5,171,851

[45] Date of Patent: Dec. 15, 1992

[54] IMIDAZOLE SUBSTITUTED BENZOXAZINE OR BENZOTHIAZINE DERIVATIVES

[75] Inventors: Moohi Y. Kim; Hyun T. Shin; Choon W. Lee, all of Seoul; Joon W. Kim, Kyungki; Soon H. Kim, Kyungki; Youngmoon Choi, Seoul; Moon H. Son, Kyungki, all of Rep. of Korea

[73] Assignee: Dong-A Pharm. Co., Ltd., Seoul, Rep. of Korea

[21] Appl. No.: 674,183

[22] Filed: Mar. 25, 1991

[30] Foreign Application Priority Data

Mar. 24, 1990 [KR] Rep. of Korea .................. 90-3989

[51] Int. Cl.$^5$ .................. C07D 413/02; C07D 413/10; C07D 417/02; C07D 417/10
[52] U.S. Cl. .................................. 544/50; 544/92
[58] Field of Search .................... 544/50, 92

[56] References Cited

U.S. PATENT DOCUMENTS 4,728,653 3/1988 Campbell et al. .................. 514/312

OTHER PUBLICATIONS

Drugs, 33; 503-519 (1987), Weber et al.

Primary Examiner—Mukund J. Shah
Assistant Examiner—Philip I. Dalton
Attorney, Agent, or Firm—Birch, Stewart, Kolasch & Birch

[57] ABSTRACT

A benzoxazine or benzothiazine derivative of the formula (A),

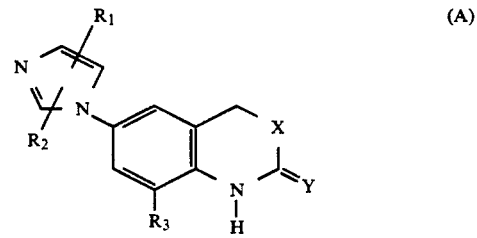

wherein $R_1$, $R_2$ and $R_3$ are the same or different and represent a hydrogen atom or a $C_{1-4}$ alkyl group; or $R_1$ and $R_2$ can be joined together along with the imidazole ring to form a benzimidazole; X and Y are the same or different and represent an oxygen or sulfur atom; or a pharmaceutically acceptable salt thereof, exhibits an excellent inotropic effect and can be used as a cardiac stimulant.

26 Claims, No Drawings

IMIDAZOLE SUBSTITUTED BENZOXAZINE OR BENZOTHIAZINE DERIVATIVES

BACKGROUND OF THE INVENTION

1. Field of the Invention

This invention relates to benzoxazine or enzothiazine derivatives which have cardiac stimulant activity by positive inotropic action. The compounds are useful in the treatment of cardiac disease in particular heart failure.

According to the present invention, there are provided novel benzoxazine or benzothiazine derivatives of the formula (A) and their pharmaceutically acceptable salts:

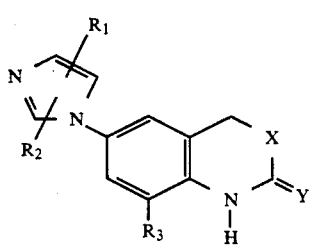

(A)

wherein X and Y which are the same or different and represent oxygen or sulfur atom; $R_1$, $R_2$, and $R_3$ which are the same or different and represent hydrogen atom, $C_1$–$C_4$ lower alkyl group, or $R_1$ and $R_2$ may be connected to form a fused aromatic homocycle or heterocycle.

2. Description of Prior Arts

As drugs which increase myocardial contraction, that is, slow inotropic action, cardiac glycosides have been used for about past 200 years. However digitalis preparations have a narrow safety margin and also have a problem of insufficient curative effect.

As another class of positive inotrope, isoproterenol, dopamine and dobutamine which act on the sympathetic nervous system have been used. However, these drugs increase heart rate and have a risk of causing arrhythmia and moreover, have the disadvantage that they should be used in the form of i.v. injection. Therefore, the drugs are not proper for the treatment of chronic congestive heart failure (Drugs, 1987, 33, 503).

So, the study has been focused on drugs which show positive inotropic action, can be administered orally and have a broad safety margin.

In U.S. Pat. No. 4,728,653, a quinolone cardiac stimulant of the following general formula (1)

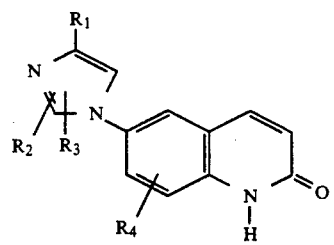

(1)

wherein $R_1$, $R_2$ and $R_3$ represent $C_{1-4}$ lower alkyl group, lower alkoxy group, halogen atom, hydroxymethyl group or nitro group, and $R_4$ represents $C_{1-4}$ lower alkyl group or halogen atom is described.

The present inventors have carried out an intensive study and surprisingly found out that the novel benzoxazine or enzothiazine derivatives of formula (A) or salts thereof have a cardiac stimulant effect by positive inotropic action.

SUMMARY OF THE INVENTION

Accordingly, one object of the present invention is to provide the novel benzoxazine or benzothiazine derivatives of the formula (A) and their pharmaceutically acceptable salts which do not act on sympathetic nervous system but show positive inotropic action.

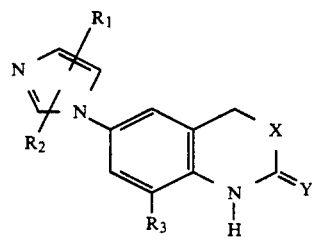

(A)

wherein X and Y which are the same or different, represent oxygen or sulfur atom; $R_1$, $R_2$, and $R_3$ which are the same or different and represent hydrogen atom, $C_{1-4}$ lower alkyl group, or $R_1$ and $R_2$ may be connected to form a fused aromatic homocycle or eterocycle.

Another object of the present invention is to provide a process for the preparation of the novel benzoxazine or benzothiazine derivatives of the formula (A) and pharmaceutically acceptable salts.

The novel compounds of the formula (A) may be prepared by the following procedures.

(Scheme I):

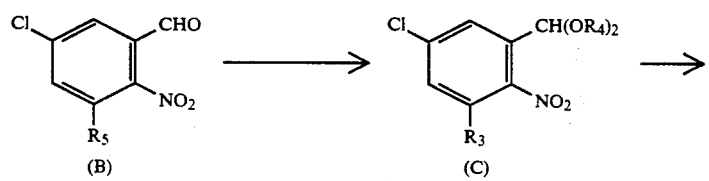

(Scheme I):

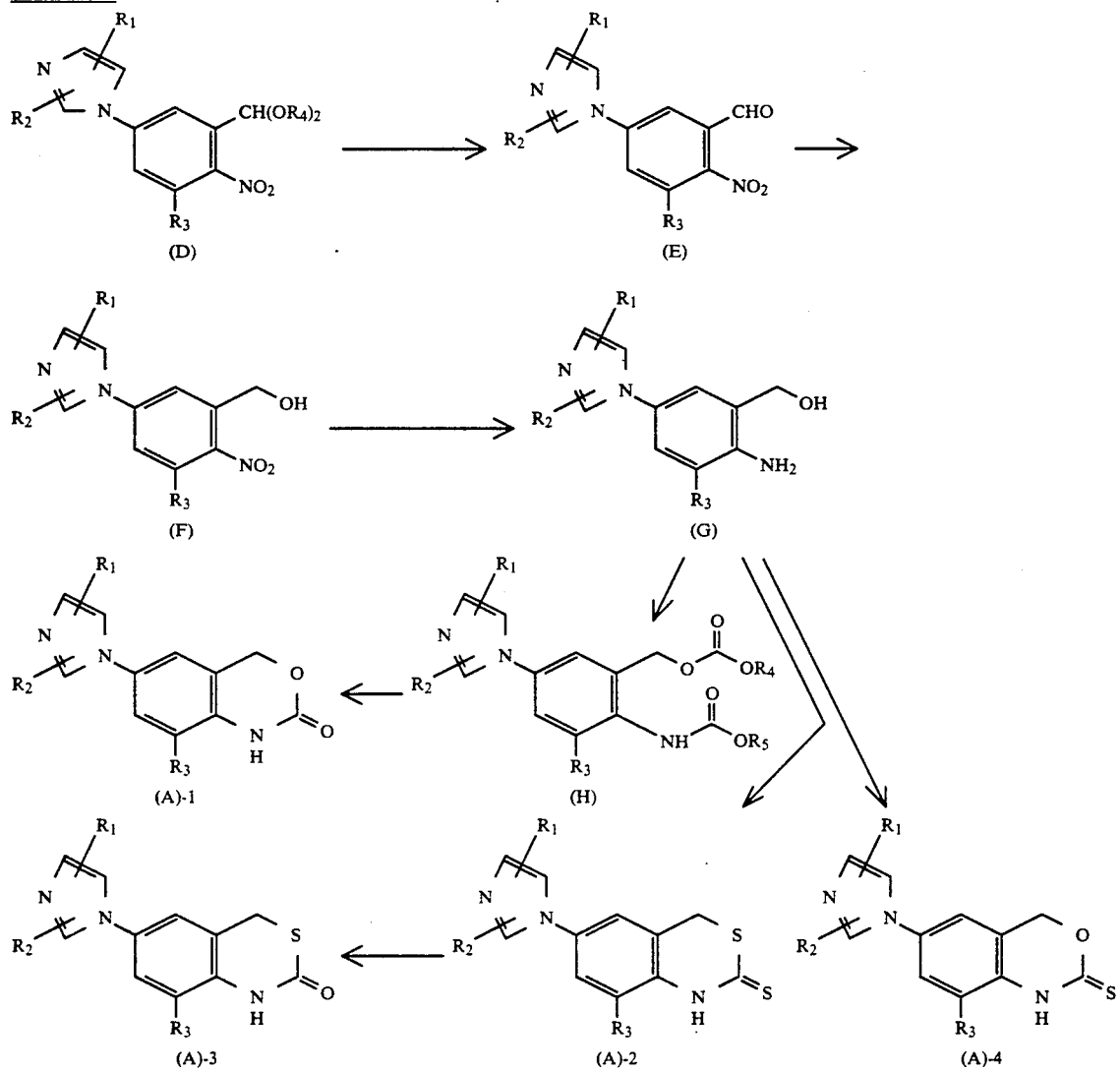

wherein $R_1$, $R_2$ and $R_3$ are the same as defined above and $R_1$ and $R_2$ which are the same or different represent $C_1$–$C_2$ lower alkyl group.

The known compound (B) can be converted to its acetal (C) by treatment with a suitable alcohol in the presence of a catalytic amount of acid. The compound (D) may be prepared by heating a compound (C) with a substituted imidazole in a proper solvent under high temperature.

As solvent which may be used in this reaction, dimethylsulfoxide, N,N-dimethylformamide or xylene which have comparatively high boiling point is desirable.

The reaction may be carried out under the temperature between room temperature and boiling point of the solvent used but it is desirable that the reaction is carried out at the pointing point of the solvent used. The reaction may be completed within 30 hours–48 hours.

It is desirable that the reaction is carried out under normal pressure.

The compound (E) may be prepared by acid hydrolysis of the compound (D) in a mixed solvent of water and lower alkylalcohol.

In this reaction $C_{1-5}$ lower alcohol such as methanol, ethanol or isopropanol is used and strong acid such as conc. HCl is used.

A substituted benzylalcohol of the formula (F) may be prepared by reducing a compound of the formula (E) with a common reducing agent such as sodium borohydride in a solvent such as $C_{1-5}$ lower alcohol, e.g. methanol, ethanol, etc., ether such as tetrahydrofuran or dioxane, or any other organic solvent.

An amino alcohol derivative of the formula (G) may be prepared by catalytic hydrogenation of the compound (F) with metal catalyst such as palladium under hydrogen atmosphere.

A carbonate derivative (H), the precursor of the final product may be obtained by stirring the compound of the formula (G) with an agent which can introduce the C=Y group such as an alkyl haloformate e.g. ethyl chloroformate or N,N-thiocarba mylimidazole in the presence of acid scavinger such as amine, e.g., triethylamine, trimethyamine or pyridine in a inert solvent such as dichloromethane or any other inert solvent under room temperature.

A benzoxazine derivative (A)-1 of the object compound may be obtained by stirring the compound of the formula (H) with excess metal alkoxide such as 28% sodium alkoxide in alcohol solution under room temperature.

Another object compound (A)-2 may be obtained by heating the mixture of a compound of the formula (G) with potassium ethyl xanthate.

A third object compound (A)-3 may be obtained by treatment with hydrogen peroxide to the compound (A)-2 under basic condition.

A fourth compound (A)-4 may be obtained by stirring the aminobenzylalcohol (G) with N,N-thiocarbonylimidazole in a solvent such as lower ketone under heating.

As another method of the preparation of the compound (A) (Scheme II), a compound of the formula (I) is reacted with imidazole derivative to give a compound of the formula (J), by reducing the compound of the formula (J) like the said method to give a compound of the formula (K), by introducing iodine to the ortho-position of amino group of the compound of the formula (K) to give a compound of the formula (1), by substituting the iodine with CN group to give a compound of the formula (M), by reducing the CN group to give a compound of the formula (N), and by reducing the compound of the formula (N) like the said method to give a compound of the formula (G). The compound of the formula (A) may be obtained by treating the compound of the formula (G) with the analogy method of the said methods (Scheme I).

The followings are the scheme (II).

(Scheme II)

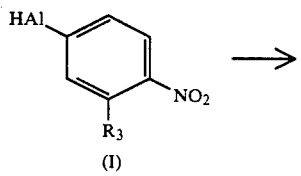
(I)

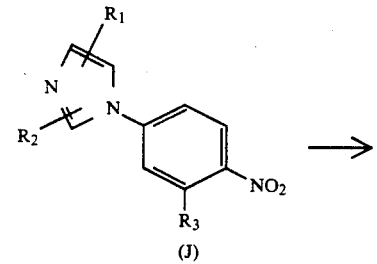
(J)

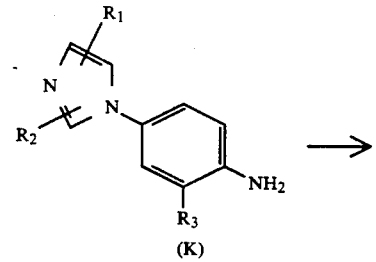
(K)

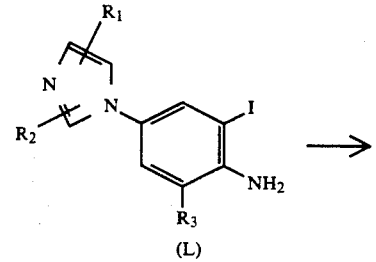
(L)

(Scheme II)
-continued

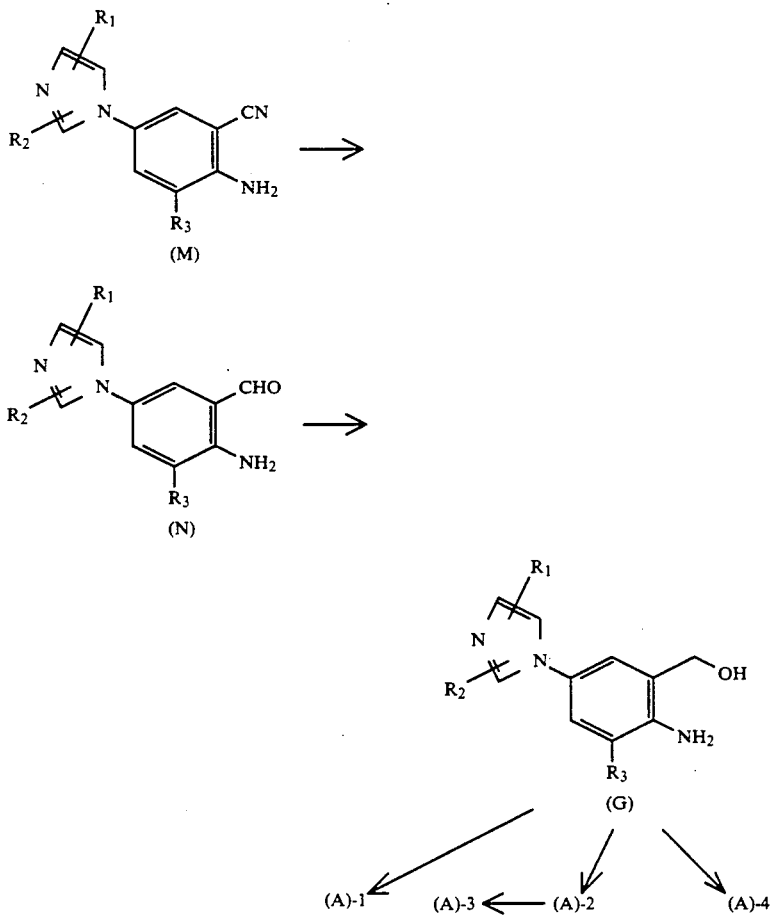

wherein $R_1$, $R_2$, and $R_3$ are the same defined above, and Hal is a halogen atom.

A compound of the formula (J) may be obtained by reacting a known compound of the formula (I) with an imidazole compound.

A compound of the formula (K) may be obtained by reducing the compound of the formula (J) under hydrogen atmosphere in the presence of metal catalyst.

A compound of the formula (L) may be obtained by introducing iodine on the ortho-position of the amino group of the compound of the formula (I) with iodinemonochloride in acetic acid at room temperature.

The aminobenzylalcohol derivative (G) may be obtained through the compound (M) and the compound (N) with 3 steps of procedures of the reaction of KCN in the presence of Palladium catalyst, addition of hydride with diiobutyl aluminum hydride and reduction with sodium borohydride.

The benzoxazine of benzothiazine derivatives (A) may be obtained from the amino benzylalcohol derivative (G) by the same procedures with the Scheme I.

The present invention will be explained with the following examples but these examples do not restrict the present invention.

EXAMPLE 1

Preparation of of 5-chloro-2-nitrobenzaldehyde diethyacetal

A mixture of 5-chloro-2-nitrobenzaldehyde (5.0 g), toluene (50 ml), p-toluenesulfonic acid monohydrate (25 mg) was heated under stirring for 2 hours by dehydrating water which was formed in the course of reaction. The solvent was distilled under reduced pressure and the residue was column chromatographed (hexane/ethyl acetate: 8/1) to give 6.5 g of the pure title compound (93%).

NMR(CDCl$_3$): 0.71(t, 6H), 3.04–3.23(m, 4H), 5.50(s, 1H), 6.90(d-d, 1H), 7.28(d, 2H).

EXAMPLE 2

Preparation of 5-(2-methylimidazol-1-yl)-nitrobenzaldehyde diethylacetal

To a solution of xylene (2 ml) and NaH (212 mg) were added dropwise a mixture solution of 5-chloro-2-nitroenzaldehyde diethylacetal (2.29 g), 2-methylimidazole (724 mg) and dimethylsulfoxide (30 mg). The mixture was heated under stirring for 24 hours at 100° C. The solvent was distilled under reduced pressure. To the residue was added water. The mixture was extracted with dichloromethane and the extract was dried with Na$_2$SO$_4$ and filtered. The filtrate was distilled to give a residue.

The residue was column chromatographed (methanol/chloroform: 1/20) to give 3.0 g of the pure product (78%).

NMR (CDCl$_3$): 1.19(t, 3H), 2,37(s, 3H), 3.68(m, 6H), 6.02(s, 1H), 7.01(s, 2H), 7.36(d-d, 1H), 7.74(d, 1H), 7.90(d, 1H).

EXAMPLE 3

Preparation of 5-(2-methylimidazol-1-yl)-2-nitrobenzaldehyde

A mixture of 5-(2-methylimidazol-1-yl)-2-nitrobenzaldehyde diethyacetal (735 mg), conc-HCl (2.0 ml), water (4.0 ml) and isopropyl alcohol (4.0 ml) was heated under stirring for 1 hour and cooled. The mixture was extracted with dichloromethane and the extract was dried with Na$_2$SO$_4$ and filtered. The filtrate was distilled to give 494 mg (88%) of the title compound.

NMR (DMSO-d$_6$): 2.37(s, 3H), 6.99(d, 1H), 7.50(d, 1H), 7.90(d, 1H, 8.00(d-d, 1H), 8.30(d, 1H), 10.27(s, 1H).

EXAMPLE 4

Preparation of 5-(2-methylimidazol-1-yl)-2-nitrobenzylalcohol

To a solution of 5-(2-methylimidazol-1-yl)-2-nitrobenzaldehyde (349 mg) and methanol (5.0 ml) was added slowly sodium borohydride (114 mg) at 0° C. and the mixture was stirred at room temperature for 4 hours. Methanol was distilled at reduced pressure to give a residue. Water was added to the residue and the mixture was stirred at room temperature for 30 minutes, filtered and dried to give 360 mg (100%) of the title compound.

NMR(Methanol-d$_6$): 2.40(s, 3H), 5.00(s, 2H), 7.00(d, 1H), 7.27(d, 1H), 7.54(d-d, 1H), 7.88(d. 2H), 8.24(d, 1H).

EXAMPLE 5

Preparation of 2-amino-5-(2-methylimidazol-1-yl)benzylalcohol

A mixture of 5-(2-methylimidazol-1-yl)-2-nitrobenzylalcohol (308 mg), 10% Pd/C(84 mg) and methanol (5.0 ml) was hydrogenated at 1.atmosphere. The mixture was stirred at room temperature for 2 hours and filtered to remove the catalyst. The filtrate was diltilled under reduced pressure to give 268 mg (100%) of the title compound.

NMR (CDCl$_3$): 2.18(s, 3h), 3.44(s, 2H), 4.45(b, 1H), 4.65(s, 2H), 6.69(d, 1H), 6.85(s, 2H), 6.91(s, 2H).

EXAMPLE 6

Preparation of ethyl 2-ethoxycarbonylamino-5-(2-methylimidazol-1-yl)benzylcarbonate To a solution of 2-amino-(2-methylimidazol-1-yl)benzylalcohol (243 mg), pyridine (0.21 ml) and dichloromethane (4.0 ml) was dropwise added ethylchloroformate (0.25 ml) at 0° C. and the mixture was stirred at room temperature for 12 hours. To the mixture was added water and the reaction mixture was extracted with dichloromethane and the extract was dried with Na$_2$SO$_4$ and filtered. The filtrate was distilled to give a residue. The residue was column chromatographed (methanol/chloroform: 1/20) to give 296 mg of the title compound.

NMR(CDCl$_3$): 1.26(m, 2H), 2.28(s, 3H), 4.18(m, 4H), 5.11(s, 6H), 6.94(d, 1H), 6.98)d, 2H), 7.82(s, 1H), 7.92(d, 1H).

EXAMPLE 7

Preparation of 6-(2-methylimidazol-1-yl)-(4H)-3,1-benzoxazine-2-one

Ethyl 2-ethoxycarbonylamino-6-(2-methylimidazol-1-yl)benzylcarbonate (260 mg) was dissolved in methanol (5.0 ml) and excessive 28% sodium methoxide in methanol was added thereto at 0° C. The mixture was stirred at room temperature for 30 minutes. Solvent was distilled under reduced pressure and water was added thereto.

The mixture was extracted dichloromethane, dried with Na$_2$SO$_4$ and distilled to give 128 mg (75%) of the title compound.

NMR(DMSO-d$_6$): 2.23(s, 3H), 5.30(s, 2H), 6.86(d, 1H), 6.95(d, 1H), 7.28(s, 2H).

EXAMPLE 8

Preparation of 6-(4-methylimidazol-1-yl)-(4H)-3,1-benzothiazin-2-one

A mixture of 2-amino-5-(4-methylimidazol-1yl)benzylalcohol (835 mg), potassium ethyl xantate (7.90 g) and dimethylformaldehyde (50 ml) was heated under stirring under the nitrogen atmosphere at 100° C. for 22 hours. Solvent was distilled under reduced pressure to give a residue. Water was added to the residue and the mixture was extracted with ethylacetate. The extract was dried with Na SO and filtered. The solvent was removed to give 750 mg (70%) of the title compound.

NMR(DMSO-d$_6$): 2.14(s, 3H), 4.16(s, 2H), 7.26(d, 1H), 7.38(br, 1H), 7.51–7.58(m, 2H), 8.08(br, 1H), 12.62(br, 1H).

EXAMPLE 9

Preparation of 6-(4-methylimidazol-1-yl)-(4H)-3,1-benzothiazin-2-one

A mixture of 6-(4-methylimidazol-1-yl)-I4H)-3,1-benzothiazin-2-one HCl (390 mg), 1M sodium hydroxide solution (30 ml) and 3% hydrogen peroxide solution (25 ml) was stirred at room temperature for 2.5 hours and the reaction mixture was extracted with dichloromethane, dried with Na$_2$SO$_4$ and filtered. The solvent was removed to give 180 mg (56%) of the title compound.

NMR(DMSO-d$_6$): 2.14(s, 3H), 4.22(s, 2H), 7.05(d, 1H), 7.39(s, 1H), 7.45(d-d, 1H), 7.55(d, 1H), 8.05(s, 1H).

EXAMPLE 10

Preparation of 5-(4-methylimidazol-1-yl)-2-nitrotoluene

A mixture of 5-fluoro-2nitrotoluene (1.05 g), 4-methylimidazole (556 mg) and sodium carbonate (753 mg) in dimethylformaldehyde (23 ml) was heated under stirring for 36 hours. The reaction mixture was distilled under reduced pressure to remove solvent. The residue was dissolved in water and the solution was acidified with 4N HCl solution to pH 5 and extracted with chloroform. The water layer was made to pH 10 with 2.5N sodium hydroxide solution, extracted with chloroform, dried with MgSO$_4$ and filtered. The solution was distilled to give 1.09 g (74%) of the title compound.

NMR(CDCl$_3$): 2.27(s, 3H), 2.66(s, 3H), 7.04(s, 1H), 7.24–7.32(m, 2H), 7.84(s, 1H), 8.11(d, 1H).

EXAMPLE 11

Preparation of
2-amino-5-(4-methylimidazol-1-yl)toluene

A mixture of 5-(4-methylimidazol-1-yl)-2-nitrotoluene (198 mg), 10% Pd/C (58 mg) and methanol (3.0 ml) was hydrogenated with hydrogen of 1 atmosphere. The mixture was stirred at room temperature for 2 hours and filtered. The filtrate was distilled under reduce pressure to give 149 mg (87.6%) of the title compound.

NMR(CDCl$_3$): 2.04(s, 3H), 2.21(s, 3H), 3.76(br, 2H), 6.60(d, 1H), 6.78–6.95(m, 3H), 7.53(d, 1H).

EXAMPLE 12

Preparation of
2-amino-3-iodo-5-(4-methylimidazol-1-yl)toluene

A mixture of 2-amino-5-(4-methylimidazol-1-yl)toluene (100 mg), iodomono-chloride (104 mg) and acetic acid (1.3 ml) was stirred at room temperature for 2 hours. Solvent was removed under reduced pressure to give a residue. The residue was made to pH 10 with saturated sodium bicarbonate solution, extracted with chloroform. The extract was dried with MgSO$_4$, filtered and removed solvent to give 68 mg (41%) of the title compound.

NMR(CDCl$_3$): 2.21(s, 6H), 4.10(br, 2H), 6.8(t, 1H), 6.99(t, 1H), 7.45(d, 1H), 7.56(d, 1H).

EXAMPLE 13

Preparation of
2-amino-3-cyano-5-(4-methylimidazol-1-yl)toluene

A mixture of 2-amino-3-iodo-5-(4-methylimidazol-1-yl)toluene (391 mg), potassium cyanide (130 mg), PD(OCA) (catalytic amount) and dimethylformaldehyde (4.01 ml) was heated under stirring under nitrogen atmosphere for 3 days. Solvent was removed to give a residue. To the residue was added water and the solution was extracted with chloroform. The extract was dried with MgSO and solvent was removed to give 175 mg (66%) of the title compound.

NMR(CDCl$_3$): 2.21(s, 3H), 2.24(s, 3H), 4.54(br, 2H), 6.83(s, 1H), 7.21(s, 2H), 7.57(s, 1H).

EXAMPLE 14

Preparation of
2-amino-3-methyl-5-(4-methylimidazol-1-yl)benzaldehyde

To a solution of 2-amino-3-cyano-5-(4-methylimidazol-1-yl)toluene (166 mg) in tetrahydrofuran (2.6 ml) was added 1.5M diisobutylaluminium hydride (1.1 ml) at 0° C. and the mixture was stirred at 40° C. for 6 hours. After the reaction was completed, 10 ml of 3N hydrogen chloride solution was added to the reaction mixture. The whole mixture was stirred for 1 hour. The mixture was bacidified with saturated sodium bicarbonate solution and was extracted with chloroform. The extract was dried with Na$_2$SO$_4$ and solvent was distilled to give 63 mg (38%) of the title compound.

NMR(CDCl$_3$): 2.21(s, 3H), 2.27(s, 3H), 6.32(br, 2H), 6.88(s, 1H), 7.23(d, 1H), 7.32(d, 1H), 9.87(s, 1H).

EXAMPLE 15

Preparation of
2-amino-methyl-5-(4-methylimidazol-1-yl)benzylalcohol 2-amino-3-methyl-5-(4-methylimidazol-1-yl)benzaldehyde (57 mg) was dissolved in methanol (1 ml) and sodiumborohydride (40 mg) was added thereto at 0° C. The mixture was stirred at room temperature for 6 hours and was distilled under reduced pressure to remove solvent. To the residue was added water. The mixture was extracted with chloroform. The extract was dried with Na$_2$SO$_4$ and distilled to give 34 mg (59%) of the title compound.

NMR(CDCl$_3$): 2.19(s, 3H), 2.21(s, 3H), 4.65(s, 2H), 6.81(s, 1H), 6.84(d, 1H), 6.93(d, 1H), 7.33(s, 1H).

EXAMPLE 16

Preparation of ethyl
2-ethoxycarbonylamino-3-methyl-5-(4-methylimidazol-1-yl)benzylcarbonate The title compound was obtained from 2-amino-3-methyl-5-(4-methylimidazol-1-yl)benzylalcohol by analogous method to the Example 6 (86%).

NMR(CDCl$_3$): 1.26(t, 6H), 2.24(s, 3H)<2.31(s, 3H), 4.10–4.23(m, 4H), 5.14(s, 2H), 6.94(s, 1H), 7.19(d, 1H), 7.24(d, 1H), 7.71(s, 1H).

EXAMPLE 17

Preparation of
8-methyl-6-(4-methylimidazol-1-yl)-(4H)-3,1-benzoxazin-2-one

The title compound was obtained from ethyl 2-ethoxycarbonylamino-3-methyl-5-(4-methylimidazol-1-yl)benzylcarbonate by analogous method to the Example 7 (87%).

NMR(Methanol-d$_6$): 2.22(s, 3H), 2.31(s, 3H), 5.24(s, 2H), 7.13(s, 1H), 7.17(s, 1H), 7.24(s, 1H), 7.89(s, 1H).

EXAMPLE 18

Preparation of
8-methyl-6-(4-methylimidazol-1-yl)-(4H)-3,1-benzothiazin-2-thione The title compound was obtained from 2-amino-5-(4-methylimidazol-1-yl)benzylalcohol by anlogous method of the Example 8 (72%).

NMR(DMSO-d$_6$): 2.14(s, 3H), 2.29(s, 3H), 4.17(s, 2H), 7.14(s, 1H), 7.32(d, 1H), 7.16(d, 1H), 8.15(d, 1H), 11.91(br, 1H).

EXAMPLE 19

Preparation of
8-methyl-6-(4-methylimidazol-1-yl)(4H)-3,1-benzothiazin-2-one

The title compound was obtained from 8-methyl-6-(4-methylimidazol-1-yl)-(4H)-3,1-benzothiazin-2-one HCl by analogous method to the Example 9 (63%).

NMR(DMSO-d$_6$): 2.14(s, 3H), 2.31(s, 3H), 4.18(s, 2H), 7.36(s, 1H), 7.40(d, 2H), 8.06(d, 1H), 10.17(s, 1H).

EXAMPLE 20

Preparation of 8-methyl-6-(4-methylimidazol-1-yl)-(4H)-3,1-benzoxazin-2-thione

A mixed solution of 2-amino-3-methyl-5-(4-methylimidazol-1-yl)benzylalcohol (135 mg), N,N'-thiocarbonyldiimidazole (116 mg) and acetone (3.1 ml) was heated under stirring under nitrogen atmosphere for 2 hours. The mixture was distilled under reduced pressure to give a residue. The residue was column chromatographed(chloroform: methanol=30:1) to give 95 mg (59.0%) of the title compound.

NMR(CDCl$_6$): 2.22(s, 3H), 2.25(s, 3H), 4.49(s, 2H), 6.84(s, 1H), 7.22(s, 2H), 7.57(s, 1H).

The following compounds were obtained by the above methods:

1. 6-(imidazol-1-yl)-(4H)-3,1-benzoxazin-2-one:
NMR(Methanol-d$_6$): 5.16(s, 2H), 6.84(d, 1H), 7.05(m, 1H), 7.15(d, 1H), 7.23(d-d, 1H), 7.40(m, 1H), 7.94(m, 1H).

2. 6-(benzimidazol-1-yl)-(4H)-3,1-benzoxazin-2-one:
NMR(Methanol-d$_6$): 5.41(s, 2H), 7.08(d, 1H), 7.12–7.36(m, 2H), 7.47–7.55(m, 3H), 7.72–7.76(m, 1H), 8.35(s, 1H).

3. 6-(4-methylimidazol-1-yl)(4H)-3,1-benzoxazin-2-one:
NMR(DMSO-d$_6$): 2.33(s, 3H), 5.35(s, 2H), 7.06(d, 1H), 7.60–7.65(m, 3H), 7.90(m, 1H), 8.32(s, 1H), 10.69(s, 1H).

4. 6-(2-ethyl-4-methylimidazol-1-yl)-(4H)-3,1-benzoxazin-2-one:
NMR(DMSO-d$_6$): 1.08(t, 3H), 2.08(s, 3H), 2.49(m, 2H), 5.30(s, 2H), 6.84(s, 1H), 6.95(d, 1H), 7.23–7.26(m, 2H), 12.51(br, 1H).

5. 6-(2,4-dimethylimidazol-1-yl)-(4H)-3,1-benzoxazin-2-one:
NMR(CDCl$_3$): 2.20(s, 3H), 2.28(s, 3H), 5.34(s, 2H), 6.64(s, 1H), 6.94(d, 1H), 7.02(d, 1H), 7.15(d-d, 1H), 10.98(s, 1H), 6. 6-(8-azabenzimidazol-1-yl)-(4H)-3,1-benzoxazin-2-one:
NMR(DMSO-d$_6$): 5.39(s, 2H), 7.05(d, 1H), 7.4(m, 1H), 7.77(s, 2H), 8.22(d-d, 1H), 8.44(d-d, 1H), 8.94(s, 1H), 10.42(s, 1H).

7. 6-(4-methylbenzimidazol-1-yl)-(4H)-3,1-benzoxazin-2-one:
NMR(CDCl$_3$): 2.72(s, 3H), 5.41(s, 2H), 7.09–7.43(m, 6H) 8.14(s, 1H), 9.09(br, 1H), 8. 6-(imidazol-1-yl)-(4H)-3,1-benzothiazin-2-thione:
NMR(DMSO-d$_6$): 4.17(s, 2H), 7.10(s, 1H), 7.30(d, 1H), 7.59–7.64(t, 3H), 8.20(s, 1H), 12.64(s, 1H), 9. 6-(imidazol-1-yl)-(4H)-3,1-benzothiazin-2-one:
NMR(DMSO-d$_6$): 4.23(s, 2H), 7.09(t, 2H), 7.50–7.65(m, 3H), 8.16(s, 1H), 10.88(s, 1H).

10. 8-methyl-6-(4-methylimidazol-1-yl)-(4H)-3,1-benzothiazin-2-one:
NMR(DMSO-d$_6$): 2.34(s, 3H), 2.45(s, 3H), 4.16(s, 2H), 7.65(s, 1H), 7.95(d, 1H), 9.55(d, 1H), 11.85(s, 1H).

11. 8-methyl-6-(imidazol-1-yl)-(4H)-3,1-benzoxazin-2-one:
NMR(CDCl$_3$): 2.23(s, 3H), 5.32(s, 2H), 7.05(d, 1H), 7.20(d, 1H), 7.25(d, 1H), 7.42(d, 1H), 7.90(s, 1H), 9.82(br, 1H).

12. 8-methyl-6-(imidazol-1-yl)-(4H)-3,1-benzothiazin-2-one:
NMR(CDCl$_3$): 2.14(s, 3H), 4.16(s, 2H), 7.20(s, 2H), 7.40(m, 2H), 7.69(m, 1H), 9.85(s, 1H), 13. 8-methyl-6-(imidazol-1-yl)-(4H)-3,1-benzothiazin-2-thione:
NMR(CDCl$_3$): 2.23(s, 3H), 4.16(s, 2H), 7.15(d, 1H), 7.27(d, 1H), 7.48–7.55(d, 1H), 8.11(s, 1H), 10.91(br, 1H).

14. 6-(2,4-dimethylimidazol-1-yl)-(4H)-3,1-benzothiazin-2-one:
NMR(CDCl$_3$): 2.22(s, 3H), 2.36(s, 3H), 4.23(s, 2H), 6.65(d, 1H(, 6.89)s, 3H), 4.23(s, 2H), 12.01(s, 1H), 15. 6-(2,4-dimethylimidazol-1-yl)-(4H)-3,1-benzothiazin-2-thione:
NMR(DMSO-d$_6$): 2.22(s, 3H), 2.36(s, 3H), 4.16(s, 2H), 7.09(m, 2H), 6.92(s, 1H), 9.92(s, 1H), 16. 8-methyl-6-(2,4-dimethylimidazol-1-yl)-(4H)-3,1-benzoxazin-2-one:
NMR(DMSO-d$_6$): 2.13(s, 3H), 2,21(s, 3H), 2.36(s, 3H), 5.42(s, 2H), 6.69(d, 1H), 6.92(d, 1H), 7.05(d, 1H), 7.28(d-d, 1H), 10.65(s, 1H), 17. 8-methyl-6-(2,4-dimethylimidazol-1-yl)-(4H)-3,1-benzthiazin-2-one:
NMR(DMSO-d$_6$): 2.14(s, 3H), 2.29(s, 3H), 2.38(s, 3H), 4.31(s, 2H), 6.71(s, 1H), 7.68(m, 2H), 10.48(s, 1H), 18. 8-methyl-6-(2,4-dimethylimidazol-1-yl)-(4H)-3,1-benzothiazin-2-thione:
NMR(DMSO-d$_6$): 2.12(s, 3H), 2.23(s, 3H), 2.36(s, 3H), 4.18(s, 2H), 7.26(s, 3H), 2.36(s, 3H), 7.72(d, 1H), 10.16(s, 1H).

A free base form and a acid addition salt form of the compound of the formula (A) are both useful. The acid addition salt of the compound (A) is the from which is useful as drug and may be prepared by adding an acid to the free base form of the compound (A). An acid which is useful in the present invention should be such acid that can form an acid addition salt this is pharmaceutically acceptable salt.

A pharmaceutically acceptable salt means that anion of the salt does not harm on an animal tissue at a curative dose. That is, the useful cardiac action of the present compound must not be lowered by side effect causes by the anion. As a useful acid addition salt, hydrochloride, sulfate, phosphate or methanesulfonate of the compound(A) is preferred.

However, as pharmaceutically acceptable salt within the present invention, there may be referred inorganic salt such as sulfate, phosphate or hydrochloride, and organic salt such as metanesulfonate, lactate, sulfamic acid salt, acetate, citrate, succinate, ethanesulfonate, cyclohexylsulfamate or kinic acid salt of the present compound(A).

The acid addition salt of the present invention may be prepared by the following methods.

Firstly: In a suitable solution such as a suitable acid-containing water solution or water-alcoholic solution is dissolved a free base of the present compound and then the acid addition salt is separated by concentrating the solution; and Secondly: A free base is reacted with an acid in a suitable solvent and then the acid addition salt is directly separates or is separated by concentrating the solution. All of the said acid addition salts of the basic compound of the present compound come within the present invention.

Molecular structure of the compound of the formula (A) of the present invention is confirmed by IR spectrophotometry, UV spectrophotometry, visible ray spectrophotometry, NMR spectrography, Mass spectrography and the comparison between the calculated and found elementary analysis.

The compound of the formula (A) can be used as a form of routine pharmaceutical preparations. Actually, the present compound can be administered in the form of various oral or parentaral preparations. In preparing pharmaceutical preparations, diluting agents or additives such as filling agents, extending agents, binding agents, wetting agents, disintegrating agents, surfactants or the like may be used.

For oral administration, solid preparation such as tablet, pill, powder, granule, or capsule is formed and used. For preparing such a said solid preparation, one or more additives such as starch, calcium carbonate, sucrose, lactose or gelatin is mixed and formulated.

In addition to the above said additives, lubricating agent such as magnesium sterate or talc may be used.

For oral administering liquid preparation, suspension, liquid, emulsion or syrup preparation is routinely used. For preparing such preparation, various additives such as wetting agent, sweetening agent, perfum, preservating agent or the like is included in addition to simple additives such as water or liquid paraffin. For parenteral administration preparation, sterilized water solution, non-water solution, suspension, emulsion or freeze-dryed preparation is formed and used. For preparing non-water solution, synthesized mineral oil such as propylenglycol or polyethyleneglycol; plant oil such as olive oil; or injectable ester such as ethyl oleate may be used.

The effectiveness as cardiac stimulant of the present compound of the formula (A) is approved by blood-perfused sino-atrial preparation of dog and in-vivo test by using cat.

Experiment 1

Determination of sinus rate on blood-perfused sino-atrial preparation: Mongrel gods of either sex weighing 7-12 kg were anesthetized with sodium pentoba rbital (30 mg/kg i.v.). Heparin ob 1000 unit/kg was administered to each animal intravenously and the animals were exsanguinated. Heart was removed and put in Krebs-Henseleit solution. Catheter was inserted into blood vessel between right coronary artery and SA nodes. Right atrium and catheter were together removed. Blood supplied from carotid artery of donor dog of either sex weighing 15-25 kg, was supplied to blood vessel cather from right coronary artery and SA node under constant blood pressure of 100 mmHG by use of Peristaltic pump. The resting tension of right atrial muscle was made to 2g. The sinus rate triggered by spontaneous contraction of atrial muscle was determined on Narco physiograph Narcotrace 4). Detailed method was reported by S. Chiba, et al. in Japanese Pharmacology 25, 433-439(1975). Doses of test compounds were injected into flowing blood in gum tube connected to the near part of the catheter inserted into right coronary artery. The effects on sinus rate were shown as percent compared with the sinus ratio prior to the injection of the test compounds. The results were shown in the Table 1.

Experiment 2

Determination of contractile power on blood perfused papillary muscle preparation:

Dogs of either sex weighing 7-12 kg were anesthetized with sodium pentobarbital (30 mg/kg, i.v.). Heparin of 1000 unit/kg was administered to each animal intravenously. The animals were exsanguinated and heart was removed. The preparation was perfused through the cannulated anterior septal artery (ASA) with arterial blood from a donor dog at constant pressure of about 100 mgHg. Donor dogs were anesthetized with sodium pentobarbital (30 mg/kg, i.v.). Heparin of 1000 units/kg was administered intravenously. The papillary muscle was stimulated with rectangular pulses of 5- ms duration and about 1.5 times the threshold voltage at a rate of 120 stimuli/min through bipolar electrodes. Resting tension was made to 2 g. The developed tension of papillary muscle was determined by Isometric tresducer. Detailed method was reporated by Matsumoto in Am J. Physiol. 218, 1459-1463 (1970). Test compound at the doses of 10-30 ul was injected in flowing blood in the gum tube connected to catheter. The inotropic effect of the test compounds was shown by change percent of developed tension compared with that prior to the administration of the test compounds. $ED_{30}$ value was determined by least-square method and the results were shown in the Table 1.

Experiment 3

Determination of cardiotonic effect on anesthetized cats: Male cats weighing about 3 kg were anesthetized with sodium pentobarbital (30 mg/kg, i.p.). The same anesthetic was infused intravenously at the does of 4 mg/kg/hr in order to maintain the anesthetic state and mechanically ventilated through a cuffed endotracheal tube, chest was opened by a midline incision and a catheter for measuring left ventricular pressure was inserted through apex into left ventricle and the left ventricular pressure was measured. LVdP/dt was determined by use of diffentiator from the left ventricular pressure. Systemic blood pressure was measured by the left femoral artery by a pressure transducer and heart rate was measured by a cardiotachometer triggered by blood pressure pulses. Test compound was injected into the femoral vein by use of cannule. After completion of the surgical procedures, the cats were allowed to recover about 30 minutes before drug administration. These compounds were dissolved in 0.9% physiological saline and diluted with saline. Solvent such as DMSO or DMF was also used, if necessary. Test compound of 0.1 ml/kg was used. Detailed method was reporated in J. Med. Chem. 30. 1279-87(1987). The results were shown in the Table 2.

Experiment 4

Assessment of effect on cyclic AMP phosphodiesterase isolated from dog's heart: Dogs weighing 10 kg were anesthetized with sodium pentobarbital and heparin was administered intravenously. Heart was removed. Two to four grams of left ventricular muscle was obtained and the tissue was rinsed in ice-cold salin. Left ventricular muscle was homogenized in 10 volumes of homogenizing buffer (Tris-HCl, pH 7.8). Homogenate was then centrifuged at 100,000 X g for 40 minutes, after which the supernatent was removed. The pellet was resuspended in homogenizing buffer, centrifuged as before and the supernatent obtained as discarded. The pellet was resuspended in 10 volumes of homogenizing buffer containing Triton X-100 and BriJ 30, and incubated overnight at 4° C. The detergent-extracted proteins were then separated by centrifugation at 100,000 X g for 40 monutes. The detergent-extracted protein was dialyzed against 70 mM sodium acetate/ 5 mM 2-mercaptoethanol (pH 6.5) for 5 hours. The dialyzed extract was applied to a DEAE-cellulose column and eluted using a 70–1000 mM sodium acetate gradient. Appropriate fractions were pooled and concentrated using Amicon ultrafiltration cell. Following concentration, the protein was diluted with ethylene glycol and stored at $-20°$ C.

Phosphodiesterase activity was measured in a reaction medium (40 mM Tris-Hcl, pH 8.0). The concentration of substrate was 1.0 uM. The IC 50 values (concentration which produced 50% inhibition of substrate hydrolysis) for the various compounds examined were determined from concentration-response curves. Detailed method of this experiment was reporated in J. Mol. Cell Cardiol. 19, 1025–1036 (1987). The results were shown in the Table 3.

Experiment 5

Acute toxicity test in mice:

Acute toxicity test of 6-(4-methylimidazol-1-yl)-(4H)-3,1-benzothiazine-2-thione was conducted in BALB/C mice. The test compound was suspended in 5% arabic gum solution and administered orally to five mice at a dose of 200 mg/kg body weight by gastric tubing. In results, no dead animal was found. Accordingly, $LD_{50}$ of the compound is 200 mg/kg or more. In addition, 8-methyl-6-(4-methylimidazol-1-yl)-(4H)-3,1-benzothiazin-2-one which has the same nucleous is expected to have similar acute toxicity.

Experiment 6

Acute toxicity test of 6-(4-methylimidazol-1-yl)-(4H)-3,1-benzothiazin-2-one was conducted in ICR mouse. The test compound was dissolved in a mixed solvent of saline and DMF (2:1) and was administered intravenously to five mice at a dose of 30 mg/kg body weight. In results, no dead animal was found. Accordingly, $LD_{50}$ of the compound is 30 mg/kg or more. In addition, 8-apxlf-6-(4-methylimidazol-1-yl)-(4H)-3,1-benzothiazin-2-thione which has the same nucleous is expected to have similar acute toxicity.

Experiment 7

Acute toxicity test of 6-(4-methylimidazol-1-yl)-(4H)-3,1-benzoxazin-2-one was conducted in Spraque-Dawley rats. The test compound was suspended in 5% arabic gum and was administered orally to six rats at a dose of 300 mg/kg body weight. In results, no dead animal was found. Accordingly, LD 50 of the compound is 300 mg/kg or more. In addition, 8-methyl-6-(4-methylimidazol-1-yl)-(4H)-3,1-benzoxazin-2-one which has the same nucleous is expected to have similar acute toxicity.

TABLE 1

Pharmacological data of 6-(4-methylimidazol-l-yl)-(4H)-3,1-benzoxazin-2-one and other various compounds:

| compounds | dose (ug) | change of contractivity (%) | change of sinus rate (%) |
| --- | --- | --- | --- |
| 6-(imidazol-1-yl)- | 1.0 | +3.33 | +0.0 |
| (4H)-3,1-benzoxa- | 3.0 | +6.95 | +0.84 |
| zin-2-one | 10.0 | +9.76 | +2.52 |
|  | 30.0 | +16.24 | +6.67 |
|  | ED 30 > 1000 ug | — | — |
| 6-(benzimidazol-1- | 1.0 | +0.0 | +0.0 |
| yl)-(4H)-3,1-benz- | 3.0 | +1.13 | +0.0 |
| oxazin-2-one | 10.0 | +2.63 | +0.30 |
|  | 30.0 | +5.24 | +0.75 |
|  | ED 30 > 1000 ug | — | — |
| 6-(2-methylimidaz- | 1.0 | +0.0 | +0.0 |
| ol-1-yl)-(4H)-3, | 3.0 | +2.44 | +0.0 |
| 1-benzoxazin-2-one | 10.0 | +8.57 | +0.86 |
|  | 30.0 | +13.51 | +3.42 |
|  | ED 30 > 1000 ug | — | — |
| 6-(4-methylimidaz- | 1.0 | +2.94 | +0.0 |
| ol-1-yl)-(4H)-3,1- | 3.0 | +13.04 | +2.52 |
| benzoxazin-2-one | 10.0 | +30.43 | +5.04 |
|  | ED 30: 10.4 ug | +30.00 | +5.17 |
| 6-(2-ethyl-4-meth- | 1.0 | +0.68 | +0.00 |
| ylimidazol-1-yl)- | 3.0 | +3.45 | +0.00 |
| (4H)-3,1-benzoxazin- | 10.0 | +12.50 | +0.83 |
| 2-one | 30.0 | +14.71 | +1.65 |
|  | ED 30: 269 ug | +30.00 | +6.82 |
| 6-(2,4-dimethylim- | 1.0 | +0.0 | +0.0 |
| idazol-1-yl)-(4H)- | 3.0 | +3.70 | +0.0 |
| 3,1-benzoxazin-2- | 10.0 | +10.34 | +0.0 |
| one | 30.0 | +15.15 | +1.67 |
|  | ED 30: 81.89 ug | +30.00 | +2.56 |
| 8-methyl-6-(4,met- | 0.1 | +4.3 | +0.8 |
| hylimidazol-1-yl)- | 0.3 | +8.7 | +1.7 |
| (4H)-3,1-benzoxaz- | 1.0 | +23.9 | +6.6 |
| in-2-one | 3.0 | +79.2 | +5.8 |
|  | ED 30 = 1.2 | 30.0 | +5.0 |
| 8-methyl-6-(4-met- | 0.1 | +15.2 | 1.7 |
| hylimidazol-1-)- | 0.3 | +28.3 | 4.8 |
| (4H)-3,1-benzothia- | 1.0 | +75.0 | 8.3 |
| zin-2-one | ED 30 = 0.6 | 30.0 | +7.1 |
| 8-methyl-6-(4-met- | 0.1 | +1.4 | +2.5 |
| hylimidazol-1-yl)- | 0.3 | +5.0 | +1.6 |
| (4H)-3,1-benzothia- | 1.0 | +12.5 | +2.5 |
| zin-2-one | 3.0 | +26.5 | +3.3 |
|  | ED 30 = 5.0 | 30.0 | +3.5 |
| 6-(4-methylimidaz- | 1.0 | 0.0 | +1.2 |
| ol-1-yl)-(4H)-3,1- | 3.0 | 7.2 | +2.3 |

TABLE 1-continued

Pharmacological data of 6-(4-methylimidazol-1-yl)-(4H)-3,1-benzoxazin-2-one and other various compounds:

| compounds | dose (ug) | change of contractivity (%) | change of sinus rate (%) |
|---|---|---|---|
| benzothiazin-2-one | 10.0 | 20.5 | +5.0 |
|  | 30.0 | 30.7 | +5.6 |
|  | ED 30 = 27.9 | 30.0 | +5.6 |
| 6-(4-methylimidaz-ol-1-yl)-(4H)-3,1-benzothiazin-2-one | 1.0 | 0.0 | 0.0 |
|  | 3.0 | 1.5 | +2.5 |
|  | 10.0 | 11.5 | +1.6 |
|  | 30.0 | 23.3 | +3.3 |
|  | ED 30 = 77.0 | 30 | +3.0 |
| 6-(imidazol-1-yl)-(4H)-3,1-benzothiazin-2-one | 10.0 | +10.7 | 0.0 |
|  | 30.0 | +22.7 | 0.0 |
|  | 100.0 | +31.1 | 0.0 |
|  | ED 30 = 81.4 | 30 | 0.0 |
| 6-(imidazol-1-yl)-(4H)-3,1-benzothiazin-2-one | 10.0 | 13.8 | +1.7 |
|  | 30.0 | 37.7 | +3.5 |
|  | 100.0 | 76.7 | +9.5 |
|  | ED 30 = 20.0 | 30 | +3.4 |

TABLE 2

Inhibitory effect on PDE activity:

| compounds | concentrations of test compounds (uM) | | | | | | | IC 50 (uM) |
|---|---|---|---|---|---|---|---|---|
|  | 0.001 | 0.01 | 0.1 | 1 | 10 | 100 | 1000 |  |
| 6-(2-methylimidazol-1-yl)-(4H)-3,1-benzimidazol-2-one |  |  | 95.9 | 86.8 | 62.6 | 37.9 |  | 32.37 |
| 6-(2-methylimidazol-1-yl)-(4H)-3,1-benzoxazin-2-one |  |  | 95.1 | 77.5 | 51.7 | 35.8 |  | 12.79 |
| 6-(2-ethyl-4-methylimidazol-1-yl)-(4H)-3,1-benzoxanin-2-one |  |  | 89.9 | 66.5 | 39.0 | 28.1 |  | 3.98 |
| 6-(2,4-dimethylimidazol-1-yl)-(4H)-3,1-benzoxazin-2-one |  |  | 100.3 | 79.3 | 53.3 | 34.3 |  | 14.92 |
| 6-(imidazol-1-yl)-(4H)-3,1-benzoxazin-2-one |  |  | 90.7 | 86.1 | 60.0 | 41.8 |  | 31.0 |
|  |  |  | 98.4 | 74.5 | 52.2 | 28.8 |  | 12.7 |
| 6-(benzimidazol-1-yl)-(4H)-3,1-benzoxazin-2-one |  |  | 91.4 | 86.5 | 61.6 | 30.1 |  | 26.1 |
|  |  |  | 95.5 | 90.4 | 72.3 | 49.5 |  | 93.2 |
| 8-methyl-6-(4-methylimidazol-1-yl)-(4H)-3,1-benzoxazin-2-one |  |  | 91.8 | 78.6 | 61.6 | 32.3 |  | 2.40 |
| 8-methyl-6-(4-methylimidazol-1-yl)-(4H)-3,1-benzoxazin-2-one |  |  | 95.7 | 84.5 | 70.5 | 35.4 |  | 4.3 |
| 8-methyl-6-(4-methylimidazol-1-yl)-(4H)-3,1-benzoxazin-2-one |  |  | 84.7 | 62.9 | 41.4 | 15.0 |  | 4.05 |
| 6-(4-methylimidazol-1-yl)-(4H)-3,1-2-benzothiazin-2-one |  |  | 77.2 | 57.8 | 39.4 | 20.0 |  | 2.7 |
| 6-(4-methylimidazol-1-yl)-(4H)-3,1-benzothiazin-2-thione |  |  | 84.7 | 65.3 | 49.6 | 27.7 |  | 7.1 |
| 6-(imidazol-1-yl)-(4H)-3,1-benzoxazin-2-thione |  |  | 97.7 | 85.4 | 61.8 | 34.8 |  | 27.4 |
| 6-(imidazol-1-yl)-(4H)-3,1-benzothizin-2-one |  |  | 95.3 | 82.3 | 68.7 | 32.2 |  | 32.6 |

TABLE 3

| compounds | doses (mg/Kg. iv) | LVP (%) | LV dp/dt (%) | HR (%) | SBP (%) | dBP (%) | mBP (%) |
|---|---|---|---|---|---|---|---|
| 6-(4-methylimidazol-1-yl)-(4H)-3,1-benzoxzin-2-one | 0.01 | +7.69 | +29.63 | +1.25 | −4.55 | −7.14 | −6.00 |
|  | 0.03 | +23.08 | +85.19 | +1.88 | −9.12 | −10.71 | −10.25 |
|  | 0.1 | +30.77 | +112.96 | +6.25 | −15.91 | −14.29 | −15.00 |
| 8-methyl-6-(4-methylimidazol-1-yl)-(4H)-3,1-benzothiazin-2-one | 0.01 | +3.3 | +33.3 | +4.2 | +0.0 | +0.0 | +0.0 |
|  | 0.03 | +5.7 | +58.4 | +7.3 | −3.8 | −4.0 | −4.5 |
|  | 0.1 | +8.8 | +75.0 | +12.6 | −6.5 | −12.0 | −16.1 |
| 8-methyl-6-(4-methylimidazol-1-yl)-(4H)-3,1-benzothiazin-2-thione | 0.01 | +1.2 | +6.0 | 0.0 | −2.3 | −5.1 | −3.3 |
|  | 0.03 | +1.8 | +20.0 | 1.6 | −2.3 | −7.7 | −5.3 |
|  | 0.1 | +2.0 | +53.3 | 10.9 | −3.1 | −11.5 | −7.6 |
| 8-methyl-6-(4-methylimidazol-1-yl)-(4H)-3,1-benzoxazin-2-one | 0.01 | +0.1 | +20.0 | +2.0 | −1.7 | −8.5 | −5.5 |
|  | 0.31 | +1.2 | +40.0 | +4.4 | −3.4 | −14.3 | −9.3 |
|  | 0.1 | +4.4 | +50.0 | +7.5 | −6.6 | −20.0 | −13.9 |

TABLE 3-continued

| compounds | doses (mg/Kg. iv) | LVP (%) | LV dp/dt (%) | HR (%) | SBP (%) | dBP (%) | mBP (%) |
|---|---|---|---|---|---|---|---|
| 6-(4-methylimidazol-1-yl)- | 0.01 | 0.0 | +14.8 | +0.0 | −4.0 | −8.5 | −9.1 |
| (4H)-3,1-benzothiazin- | 0.03 | 0.0 | +33.3 | +0.6 | −10.0 | −14.3 | −12.5 |
| 2-one | 0.1 | 8.2 | +40.7 | +4.5 | −14.0 | −20.0 | −17.5 |
| 6-(4-methylimidazol-1-yl)- | 0.01 | 0.0 | 3.7 | 0.0 | +4.0 | +4.0 | +4.0 |
| (4H)-3,1-benzothiazin-2- | 0.03 | 0.0 | 18.5 | +2.1 | 0.0 | −4.0 | −3.0 |
| thione | 0.1 | 1.2 | 40.7 | +3.6 | −4.7 | −14.0 | −10.0 |
| 6-(imidazol-1-yl)-(4H)- | 0.01 | 2.0 | +8.3 | −1.1 | +2.0 | −3.2 | −2.0 |
| 3,1-benzothiazin-2-thione | 0.03 | 4.0 | +16.6 | −0.8 | +3.0 | −3.3 | +0.0 |
|  | 0.1 | 5.7 | +25.0 | +0.6 | +3.0 | −7.4 | −3.6 |
| 6-(imidazol-1-yl)-(4H)- | 0.01 | 0.0 | 0.0 | +1.6 | −2.4 | +0.0 | −1.2 |
| 3,1-benzothiazin-2-one | 0.03 | 9.9 | +20.0 | +4.7 | −4.8 | −7.8 | −5.8 |
|  | 0.1 | 18.9 | +39.6 | +7.0 | −19.1 | −19.1 | −19.6 |

What we claim is:

1. A benzoxazine or benzothiazine derivative of the formula (A) or a pharmaceutically acceptable acid addition salt thereof

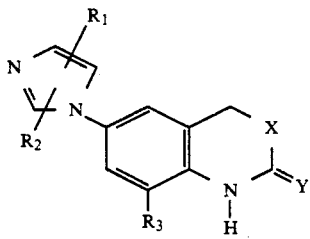

wherein X and Y are the same or different and represent oxygen or sulfur; $R_1$, $R_2$ and $R_3$ are the same or different and represent hydrogen or a $C_1$-$C_4$ alkyl group; or $R_1$ and $R_2$ can be connected together along with the imidazole ring to form a benzimidazole ring.

2. A compound according to the claim 1 in which $R_1$ represents hydrogen atom or $C_1$-$C_4$ lower alkyl group.

3. A compound according to the claim 1 in which X and Y represent oxygen or sulfur atom and complete a basic skeleton selected from the group consisting of:
1) (4H)-3,1-benzoxazine-2-one,
2) (4H)-3,1-benzoxazine-2-thione,
3) (4H)-3,1-benzoxazine-2-one, and
4) (4H)-3,1-benzoxazine-2-thione.

4. 6-(2-methylimidazol-1-yl)-(4H)-3,1-benzoxazin-2-one or pharmaceutically acceptable acid addition salt according to the claim 1.

5. 8-methyl-6-(4-methylimidazol-1-yl)-(4H)-3,1-benzoxazin-2-one or pharmaceutically acceptable acid addition salt according to the claim 1.

6. 6-(4-methylimidazol-1-yl)-(4H)-3,1-benzothiazin-2-thione or pharmaceutically acceptable acid addition salt according to the claim 1.

7. 6-(4-methylimidazol-1-yl)-(4H)-3,1-benzothiazin-2-one or pharmaceutically acceptable acid addition salt according to the claim 1.

8. 8-methyl-6-(4-methylimidazol-1-yl)-(4H)-3,1-benzothiazin-2-one or pharmaceutically acceptable acid addition salt according to the claim 1.

9. 6-(imidazol-1-yl)-(4H)-3,1-benzoxazin-2-one or pharmaceutically acceptable acid addition salt according to the claim 1.

10. 6-(benzimidazol-1-yl)-(4H)-3,1-benzoxazin-2-one or pharmaceutically acceptable salt according to the claim 1.

11. 6-(4-methylimidazol-1-yl)-(4H)-3,1-benzoxazin-2-one or pharmaceutically acceptable acid addition salt according to the claim 1.

12. 6-(2-ethyl-4-methylimidazol-1-yl)-(4H)-3,1-benzoxazin-2-one or pharmaceutically acceptable acid addition salt according to the claim 1.

13. 6-(2,4-dimethylimidazol-1-yl)-(4H)-3,1-benzoxazin-2-one or pharmaceutically acceptable acid addition salt according to the claim 1.

14. 6-(4-methylbenzimidazol-1-yl)-(4H)-3,1-benzoxazin-2-one or pharmaceutically acceptable acid addition salt according to the claim 1.

15. 6-(imidazol-1-yl)-(4H)-3,1-benzoxazin-2-thione or pharmaceutically acceptable acid addition salt according to the claim 1.

16. 6-(imidazol-1-yl)-(4H)-3,1-benzoxazin-2-one or pharmaceutically acceptable acid addition salt according to the claim 1.

17. 8-methyl-6-(4-methylimidazol-1-yl)-(4H)-3,1-benzothiazin-2-thione or pharmaceutically acceptable acid addition salt according to the claim 1.

18. 8-methyl-6-(imidazol-1-yl)-(4H)-3,1-benzoxazin-2-one or pharmaceutically acceptable acid addition salt according to the claim 1.

19. 8-methyl-6-(imidazol-1-yl)-(4H)-3,1-benzothiazin-2-one or pharmaceutically acceptable acid addition salt according to the claim 1.

20. 8-methyl-6-(imidazol-1-yl)-(4H)-3,1-benzothiazin-2-thione or pharmaceutically acceptable acid addition salt according to the claim 1.

21. 6-(2,4-dimethylimidazol-1-yl)-(4H)-3,1-benzothiazin-2-one or pharmaceutically acceptable acid addition salt according to the claim 1.

22. 6-(2,4-dimethylimidazol-1-yl)-(4H)-3,1-benzothiazin-2-thione or pharmaceutically acceptable acid addition salt according to the claim 1.

23. 8-methyl-6-(2,4-dimethylimidazol-1-yl)-(4H)-3,1-benzoxazin-2-one or pharmaceutically acceptable acid addition salt according to the claim 1.

24. 8-methyl-6-(2,4-dimethylimidazol-1-yl)-(4H)-3,1-benzothiazin-2-one or pharmaceutically acceptable acid addition salt according to the claim 1.

25. 8-methyl-6-(2,4-dimethylimidazol-1-yl)-(4H)-3,1-benzothiazin-2-thione or pharmaceutically acceptable acid addition salt according to the claim 1.

26. 8-methyl-6-(4-methylimidazol-1-yl)-(4H)-3,1-benzoxazin-2-thione or pharmaceutically acceptable acid addition salt according to the claim 1.

* * * * *